United States Patent [19]

Choate

[11] Patent Number: 5,253,641
[45] Date of Patent: Oct. 19, 1993

[54] RESPIRATORY FILTER APPARATUS AND METHOD

[76] Inventor: Thomas V. Choate, P.O. Box 87, East Sandwich, Mass. 02537

[21] Appl. No.: 770,550

[22] Filed: Oct. 3, 1991

Related U.S. Application Data

[63] Continuation of Ser. No. 444,759, Dec. 1, 1989, abandoned.

[51] Int. Cl.⁵ ............................................. A61M 11/00
[52] U.S. Cl. ........................... 128/200.14; 128/205.12
[58] Field of Search ....................... 128/201.25, 205.12, 128/205.27, 205.28, 205.29, 716, 200.14

[56] References Cited

U.S. PATENT DOCUMENTS 3,745,991  7/1973  Gauthier et al. ................... 128/716

Primary Examiner—Edgar S. Burr
Assistant Examiner—Aaron J. Lewis
Attorney, Agent, or Firm—Richard P. Crowley

[57] ABSTRACT

A respiratory filter apparatus and method to reduce the risk of any transmission of airborne disease from a patient's respiratory effluent or sputum. The apparatus includes a housing having an air inlet and an air outlet, a motor blower to draw air into the inlet and to discharge air from the outlet, a high efficiency particulate filter within the housing to filter air between the air inlet and outlet, a flexible tube having a one and the other end, one end connected to the air inlet in the housing and the other end being a disposable, truncated face cone adapted to fit about the face of a patient, and optionally at the other end, a holder to hold a nebulizing fluid to be dispensed into the lungs of the patient whereby any respiratory effluent or sputum from the patient and nebulizing fluid are drawn into the disposable face cone by the air flow from the air inlet to the air outlet by reducing the germ transmission of disease by patient coughing to others, such as airborne tuberculosis.

14 Claims, 1 Drawing Sheet

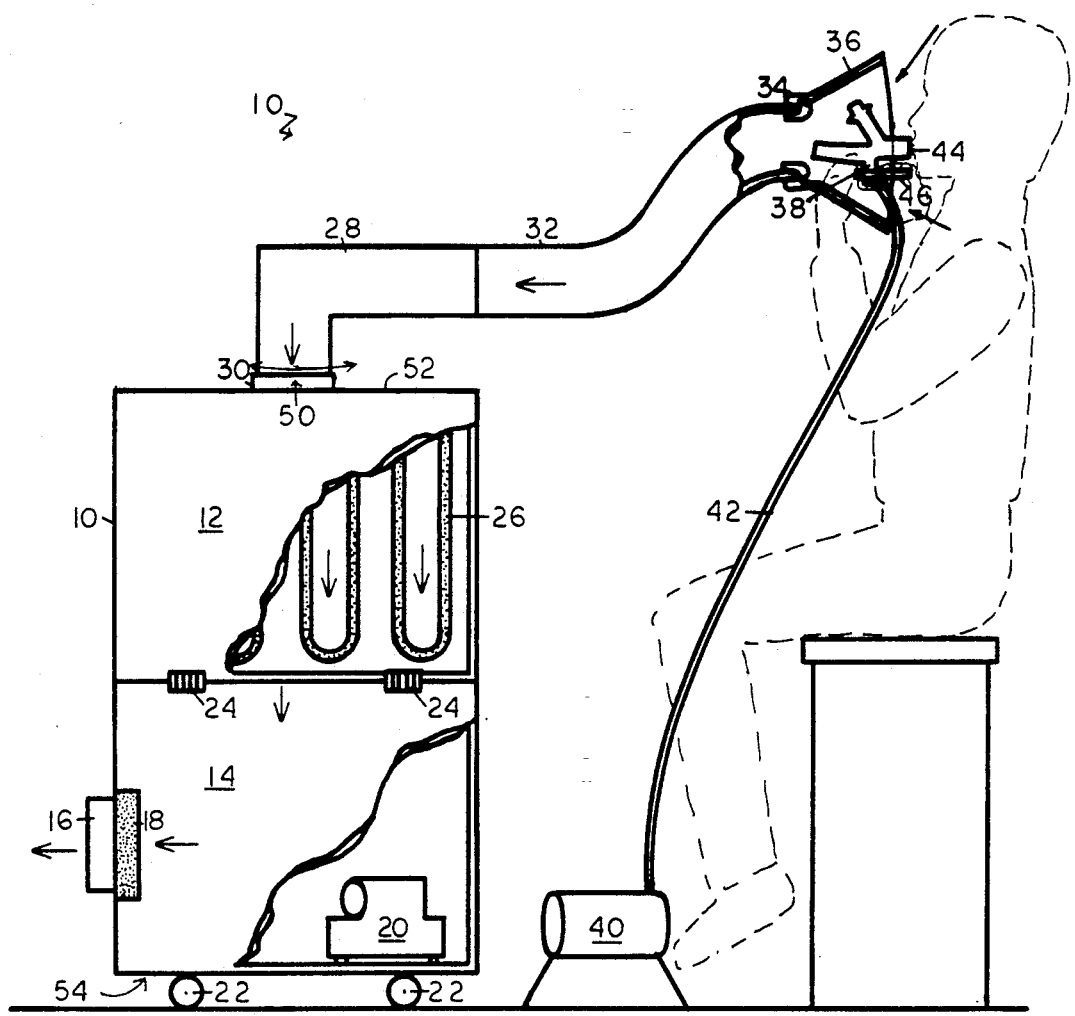

RESPIRATORY FILTER APPARATUS AND METHOD

This is a continuation of copending application Ser. No. 07/444,759 filed Dec. 1, 1989, now abandoned.

BACKGROUND OF THE INVENTION

It has been reported that extensive airborne tuberculosis transmission is associated with the treatment of patients in the process of sputum induction. In particular, extensive TB transmission has been associated with the employment of pentamadine aerosol treatments. HIV-infected patients tend to be at an increased risk of reacting to tuberculosis by virtue of aerosol airborne transmission. The transmission of the diseases to unsuspecting infected patients and to medical staff is enhanced by the coughing induced by aerosol treatments, such as pentamadine, wherein a nebulizer is connected to a free standing air compressor to generate aerosol particles of the chemical. In addition, aerosols produced by sputum induction, bronchoscopy and suctioning patients with artificial airways also may lead to the airborne transmission of diseases to other persons and staff breathing the same air. Therefore, it is desirable to remove an infectious aerosol produced by patients and also to remove airborne drug particles which may be produced when patients are treated with aerosolized forms of drugs. Typically, the medical treatments involving enhanced coughing or aerosol drug treatment of patients is carried out in rooms of adequate fresh air ventilation so as to decrease the probability of transmission. However, adequate ventilation alone cannot eliminate the risk of airborne transmission. Other techniques include carrying out the procedures in high level, ventilated areas with the air exhausted safely to the outside with negative room air pressure relative to the outside together with properly installed and maintained UV lights and with extensive and regular treatments and testing of the staff for airborne disease infection.

The hazards of airborne transmission and the occupational exposure for example to hepatitis B virus in human immunology and to other viruses has been recognized as a growing problem in occupational medicine, since the transmission of hepatitis or AIDS through sputum and saliva of a patient.

One technique for reducing the risk of airborne transmission of disease is to provide a booth approach, such as a enclosed chamber, designed to remove any infectious aerosols produced by the coughing of a patient which booth usually comprises an enclosed chamber having a seat for the patient and a back panel wall against which the patient sits and includes a prefilter, a blower and a high efficiency particulate filter. The back panel includes on its back portion a UV tube light to enclose a duct-like space and whereby on activation of the air blower, the air is drawn through the prefilter into the chamber while the patient is undergoing the aerosol treatment up over the back panel and through the duct-like space and exposed to the UV rays and through the hepafilter and then discharged into the environment.

While the booth approach may be satisfactory in some respects, the booth approach is not portable, thus it cannot be used for bedsides or non-ambulatory patients, and further is more expensive. More particularly, after treatment of the patient the booth still remains contaminated and thus there must be a period of time before the next patient can enter the enclosed booth.

It is therefore desirable to provide for a high efficiency, portable, quickly reusable respiratory filter apparatus and method.

SUMMARY OF THE INVENTION

The invention relates to a respiratory filter apparatus and method for reducing the risk of airborne disease transmission from the respiratory effluent of a patient. In particular, the invention concerns a high efficiency, particulate, portable respiratory filter apparatus employing a disposable face cone used by a patient undergoing nebulizer treatment which is likely to lead to enhanced coughing of a patient.

The invention relates to a high efficiency, respiratory filter apparatus which is designed to reduce the risk of airborne disease transmission, such as hepatitis or tuberculosis, induced from the respiratory effluent of a patient, such as by enhanced coughing of a patient during aerosol nebulizing treatment. The respiratory filter apparatus comprises a housing having an air inlet and an air outlet and which housing includes a motor blower designed to draw air into the air inlet and to discharge air from the air outlet. The apparatus includes a high efficiency, particulate filter and optionally as well an absorbent type filter, such as a charcoal filter, to absorb chemicals, such as aerosol drugs or liquid droplets, and a particulate material within the housing with one or more filters positioned within the housing to filter air between the air inlet and the air outlet. The filter apparatus also includes a tube, typically a flexible tube, say two to four inches in diameter, having a one and an other end with the one end in air passage communication with the air inlet in the housing. A disposable face cone, such as a paper or plastic, truncated face cone, is employed and secured either by clamping or fitting over the other end of the tube, and with the base of the cone extending outwardly from the other end of the tube and of sufficient size and shape to encompass generally the face of the patient using the filtering apparatus so as to gather any patient effluent, so that any respiratory effluent from the patient whose face is positioned in the face mask is drawn by the air stream from the face cone into the air inlet and through the filters to the air outlet to discharge safely into the environment.

The respiratory filter apparatus of the invention is also designed to include the employment with the face cone of a nebulizing system, and in particular, as a nebulizing chemical holder device as has been determined in many patients, particularly elderly patients, find it difficult to hold the nebulizing chemical holder while employing the nebulizer. The nebulizer holder may include an extending rod and nebulizer container holder in which to put the chemicals to be nebulized, and with the nebulizing system adapted to fit within the face cone, so that during the nebulizing aerosol treatment of the patient, which tends to induce coughing, on coughing the sputum or respiratory effluent from the patient will be drawn by the air flowing stream into the disposable face cone and the aerosols into the hepafilter and the housing. Typically, nebulizing systems employ an air compressor with a connecting tube extending into the nebulizing solution and if desired, the air compressor in use with the nebulizing system may be used or may also be placed within the housing for use to make a compact package. Typically, the face mask comprises a truncated cone made of a disposable, inexpensive material, such as paper, non-woven fibrous material, such as polypropylene or polyethylene, which may be coated or uncoated or a solid, thin plastic type material, all of which should be inexpensive or disposable and capable of being sanitized. Typically, the short end of the face cone may be slipped on the other end of the tube with a tight fit, or as desired may be clamped. However, desirably, the inner surface of the face cone should extend slightly inwardly and about the interior surface of the tube so as not to contaminate the inlet tube. Optionally and desirably the respiratory filter apparatus may include a right angle or angled swivel connector connecting the air inlet in the housing to the one end of the flexible tubing, so that the flexible tubing elbow may be swung around and positioned to meet the patient's need, either sitting or at bedside. Further, the filter apparatus has casters that roll so it may be easily removed and operated at the bedside of a patient.

In use, the patient who is subject to coughing places his face within the disposable face cone during the coughing spells and the motor blower is turned on so as to blow the aerosol contaminated sputum into and toward the hepatite filter. In addition, a patient being treated with an aerosol nebulizing system employing the nebulizing solution within the face mask, so that as the nebulizing solution induces coughing by the patient, the air flow draws the aerosol particles away from the outside environment and into the other end of the tube into the hepa-type filter.

The invention will be described for the purposes of illustration only in connection with certain preferred embodiments; however it is recognized that various changes, modifications, additions and improvements may be made to the respiratory filter as illustrated, all falling within the spirit and scope of the invention.

BRIEF DESCRIPTION OF THE DRAWING

The drawing is a schematic, illustrative, partially sectionalized drawing of a high efficiency respiratory filter apparatus of the invention in use by a patient.

DESCRIPTION OF THE EMBODIMENTS

With reference to the drawings, there is shown a hepafilter portable nebulizer apparatus having a housing 10 having an upper chamber 12 with a top surface 52 and a lower chamber 14 with a bottom surface 54 with an outlet 16 for exhaust, provided with a filter 18 and a blower 20 for blowing air out of the outlet 16 and drawing air into the upper chamber 12. The respiratory apparatus includes a plurality of wheels 22 positioned on the base or bottom surface 54 of the lower chamber 14 for the portable movement of the apparatus to a bedside location in a patient's room. The upper chamber 12 is connected to the lower chamber by a plurality of hinges 24 for movement between a closed filtration position in air-tight cooperation with lower chamber 14 and an open filter removal position to permit access to the interior space of the upper chamber 12 wherein a hepafilter of corrugated construction barrier type filter is removably disposed extending across the width of the upper chamber 12. The upper chamber includes a swivel base 30 fitting having an axis 50 for pivotable movement (see double end arrow) disposed in the central top portion of the top surface 52 thereof for rotatably connecting an upwardly extending elbow 28 of hollow tubular construction, having a 90° bend, formed of resilient material having a one end engaged in the swivel base 30 and an other end for receiving a flexible tube 32 formed of accordion type vacuum hose having an outlet end and an inlet end, the inlet end having a flange 34 being adapted to engage the conically shaped disposable face cone 36 within which is disposed a nebulizer 38. The face cone 36 is constructed of a barrier plastic material, is conically shaped having a small diameter end for engaging the flange 34 and a large diameter end for receiving the nebulizer 44 mounted on a separate, spaced apart holder 46. The nebulizer 44 is constructed to produce an aerosol medication-containing mist responsive to compressed air being introduced at the bottom of said nebulizer via a flexible air line 42 connected to an air compressor 40 located remotely to the respiratory filter apparatus and which supplies air under pressure to the nebulizer to create an aerosol to be inhaled by the patient.

Responsive to blower 20 exhausting air through outlet 16, air is drawn in (see straight, single ended arrows) passing along the walls of the disposable, conical shaped face cone 36, hence along the interior passage provided by flexible tube 32 and elbow 28 into upper chamber 12, thence be drawn through the corrugated hepafilter element thereby depositing contaminant thereon, thence into lower chamber 14 from which the air is thence exhausted through filter 18 having charcoal filter element constructed to be symmetrical with outlet 16 and adapted to provide an air tight fit with the peripheral edge thereof.

What is claimed is:

1. An efficient respiratory filter apparatus to reduce the risk of airborne disease transmission from a patient's respiratory effluent, which apparatus comprises:
   a) a housing defining an upper and lower chamber therein and the upper chamber having a top surface and having an air inlet on the top surface and an air outlet in the lower chamber and wheel means on the bottom surface of the lower chamber to permit wheeled movement of the filter apparatus;
   b) a motor blower means within the lower chamber of the housing to draw air into the air inlet and to discharge air from the air outlet;
   c) a high efficiency filter means within the housing and extending across the upper chamber to filter air drawn through the housing between the air inlet and the air outlet;
   d) a tube means having a one and an other end, one end in air passage communication with the air inlet on the top surface of the upper chamber;
   e) a face cone means secured to the other end of the tube means, the face of the cone means extending outwardly and of sufficient size and shape to encompass generally the face of the patient; and
   f) swivel means on the top surface of the upper chamber of the housing and about the air inlet and connected to the one end of the tube means to provide for swivel movement of the tube means about the axis of the air inlet to enable the convenient positioning of the face cone means for use by the patient;
   g) a nebulizer means to produce medication in aerosol form which tends to induce coughing in a patient receiving the medication whereby a patient's respiratory effluent is drawn into the cone means by the flow of air into the air inlet and aerosol particles removed by the high efficiency filter means prior to discharge of the air through the air outlet.

2. The filter apparatus of claim 1 which includes an absorbent filter means in the air outlet within the housing to absorb particles.

3. The filter apparatus of claim 2 wherein the absorbent filter means comprises a charcoal-containing filter.

4. The filter apparatus of claim 1 wherein the housing has a generally flat top surface and the air inlet is generally centrally positioned in the top surface of the housing and wherein the swivel means comprises a swivel base element mounted on the top surface about the air inlet and connected to the one end of the tube means to provide for the swivel movement of the base element and tube means about the centrally positioned air inlet.

5. The filter apparatus of claim 1 wherein the tube means comprises a generally flexible, elongated, accordion tube.

6. The filter apparatus of claim 1 wherein the face cone means includes a disposable, inexpensive, truncated cone.

7. The filter apparatus of claim 1 wherein the cone means includes a holder means to receive and hold a nebulizing solution.

8. The filter apparatus of claim 7 wherein the holder means includes an extending rod and a nebulizer container holder to retain a solution of the medication to be nebulized by the nebulizing means.

9. The apparatus of claim 1 wherein the swivel means comprises a right-angled swivel base element mounted on the said top surface for pivotable movement about the axis of the air inlet.

10. The apparatus of claim 1 wherein the nebulizing means comprises an air compressor, a nebulizer solution, holder means for the nebulizer solution and tube means to provide a flow of air from the compressor to the nebulizer solution to produce an aerosol of the nebulizer solution to induce patient coughing.

11. A method of reducing the risk of airborne disease transmission from a patient's respiratory effluent, which method comprises the steps of:
 a) providing a respiratory filter apparatus having a housing with a base swivel means having an axis and an air inlet in the top surface and an air outlet and including a high efficiency particulate filter positioned in the housing between the air inlet and the air outlet;
 b) drawing air into the air inlet and discharging air from the air outlet;
 c) filtering the air passing through the housing from the air inlet to the air outlet, so that the respiratory effluent, in the form of aerosol particles of the patient, is removed by the high efficiency particulate filter;
 d) conducting the flow of air into the air inlet by a flexible tube having a one end connected to the air inlet of the base swivel means and an other end, the other end connected to a face cone having an open end which generally encompasses the face of a patient;
 e) swiveling the base swivel means and the one end of the tube about the axis of the base swivel means and the air inlet while maintaining the housing stationary to position the face cone in a desired use position adjacent the face of the patient;
 f) placing the face of the patient in treatment generally adjacent the open end of the cone;
 g) treating the patient with an aerosol form of medication which tends to induce coughing by the patient while the face is adjacent the face cone; and
 h) drawing into the face cone by the flow of air into the air inlet aerosol particles and the respiratory effluent of the patient and filtering said particles and effluent prior to discharging the filtered air back into the environment through the air outlet.

12. The method of claim 11 which includes employing a thin, disposable face cone to receive the respiratory effluent of the patient.

13. The method of claim 11 which includes treating the patient with an aerosol form of pentamethadene.

14. The method of claim 11 which includes rolling the respiratory filter apparatus to a patient treatment position adjacent the patient, and then swiveling the face cone into a desired position.

* * * * *